United States Patent [19]

Goldenberg et al.

[11] Patent Number: 4,468,457

[45] Date of Patent: Aug. 28, 1984

[54] METHOD FOR PRODUCING A CSAP TRYPTIC PEPTIDE AND ANTI-CSAP ANTIBODIES

[75] Inventors: Milton D. Goldenberg; Dan Shochat, both of Lexington, Ky.

[73] Assignee: David M. Goldenberg, Short Hills, N.J.

[21] Appl. No.: 269,115

[22] Filed: Jun. 1, 1981

[51] Int. Cl.³ .................... C12P 21/00; C12N 9/00; A61K 39/00; A61K 39/395

[52] U.S. Cl. ..................... 435/69; 435/184; 435/272; 424/85; 424/88; 436/543

[58] Field of Search .................... 435/68, 69, 184, 272, 435/267, 543; 424/88, 85

[56] References Cited

U.S. PATENT DOCUMENTS 2,719,102 9/1955 Baldwin .................... 435/68
4,086,217 4/1978 Hansen .................... 424/88
4,228,236 10/1980 Jakstys et al. .................... 435/1

OTHER PUBLICATIONS

Sigma Chemical Co., "Biochemicals and Organic Compounds" P.O. Box 14508, St. Louis, MO 63178.
Perlmann et al., "Proteolytic Enzymes" Methods in Enzymology vol. XIX (1970) pp. 34 and 210.
Pant et al., "Further Characterization of CSAp an Antigen Associated with Gastrointestinal and Ovarian Tumors", Cancer, vol. 42 (Sep. Supplement) (9/78) pp. 1626-1634.
Shochat et al., "Isolation of Immunologically-Active Tryptic Peptides from Colon-Specific-Antigen-p (CSAp)", Proceedings American Association for Cancer Research: vol. 21 (3-1980) Abstract #886.
Beachey et al., "Repeating Covalent Structure of Streptococcal M Protein" Proceedings of the National Academy of Sciences 75(7) (1978) pp. 3163-3167.
Shochat et al., "Characterization of Colon-Specific Antigen-p and Isolation of Immunologically Active Tryptic Peptides", Journal of Immunology Vol. 126(6) (6/81) pp. 2284-2289.
Ludogovskaya et al., "Soluble Antigens of the Polyps of the Human Colon", Vop. Onkol. 13(4) (1967), pp. 39-45 Chemical Abstracts 67: 20021u.
Maisonrouge-McAuliffe et al., "Immunochemical Studies on Blood Groups", Archives of Biochemistry and Biophysics 175 pp. 71-80 (1976).
Gold et al., "Protease Digestion of Colonic Mucin", Journal of Biological Chemistry 256 (12) pp. 6354-6358 (1981).

*Primary Examiner*—Robert J. Warden
*Assistant Examiner*—J. E. Tarcza
*Attorney, Agent, or Firm*—Millen & White

[57] ABSTRACT

A tryptic peptide is produced by partial tryptic digestion of purified, high molecular size colon-specific antigen-p (CSAp), to produce a lower molecular size antigen carrying the CSAp antigenic determinant. The tryptic peptide is used to produce monospecific anti-CSAp antibodies.

19 Claims, 1 Drawing Figure

METHOD FOR PRODUCING A CSAP TRYPTIC PEPTIDE AND ANTI-CSAP ANTIBODIES

BACKGROUND OF THE INVENTION

An antigen restricted to gastrointestinal tissues and to some mucinous ovarian tumors has recently been identified. (Goldenberg et al, *Proc. Am. Assoc. Cancer Res.*, 17, 155 (1976); Pant et al, *Immunol. Commun.*, 6, 441 (1977); and Pant et al, *Cancer*, 42, 1626 (1978)). This antigen is called colon-specific antigen-p(CSAp), and is characterized by its heat-lability, phenol-sensitivity and its sensitivity to thiolic and chaotropic reagents. CSAp is immunologically distinct from other gastrointestinal antigens, including the family of phenol-soluble, heat-stable colonic organ-specific antigens called colon-specific antigens (CSA) which are found in both normal, diseased and neoplastic gastrointestinal tissues, particularly the colon and rectum. In addition, CSAp is immunologically distinct from carcinoembroyonic antigen (CEA), colonic mucoprotein antigen (CMA), zinc glycinate marker (ZGM), beta-oncofetal antigen (BOFA) and blood group antigens.

The earlier attempts to characterize CSAp suggested that the antigen has a molecular size in the range 70,000-120,000 (molecular size herein is always understood to be expressed in atomic units). However, it is now clear that native CSAp was lost during processing in these earlier experiments, and that the lower molecular weight species having CSAp antigenic activity were artifacts resulting from fragmentation of the native molecule during tissue homogenization. All previous CSAp antigenic preparations were heterogeneous mixtures of antigens having a wide range of molecular weights. These materials were difficult to purify and characterize.

The level of CSAp has been found to increase in neoplasia and in certain other diseased tissues of the colon, including morphologically normal colonic mucosa adjacent to adenocarcinoma, in Pant et al, *Cancer*, 42, 1626 (1978). Recent results indicate that CSAp is useful in the immunodiagnosis and radioimmunodetection of colorectal cancer.

A need therefore continues to exist for a method of producing a purified, immunologically active antigen having CSAp antigenic activity, and for an improved method of producing monospecific antibodies to CSAp.

OBJECTS OF THE INVENTION

Accordingly, it is an object of the present invention to provide a method for producing a purified CSAp antigen.

Another object of the present invention is to provide a method of producing monospecific antibodies to CSAp.

Upon further study of the specification and appended claims, further objects and advantages of this invention will become apparent to those skilled in the art.

SUMMARY OF THE INVENTION

The foregoing objects are achieved by providing a method for producing a purified immunologically active tryptic peptide having colon-specific antigen-p (CSAp) antigenic activity, comprising the steps of:

(a) homogenizing CSAp-containing tissue in cold 0.3-3M aqueous salt solution;

(b) centrifuging the resultant homogenate, removing the floating lipid layer, and recovering the aqueous supernatant;

(c) fractionating the recovered aqueous supernatant by gel filtration, and recovering and concentrating at least one fraction containing a CSAp having a molecular weight of about 4 million;

(d) enzymatically partially digesting the concentrated CSAp fraction with trypsin;

(e) fractionating the partial tryptic digest, and recovering at least one fraction containing a tryptic peptide having CSAp antigenic activity, having a molecular weight of about 120,000 and having substantially no absorbance at 280 nm.

In a composition of matter aspect, the present invention includes the CSAp antigen produced by the present method. The invention also includes an improved method for producing monospecific anti-CSAp antibodies using the antigen of the invention.

DETAILED DISCUSSION

Figure 1:
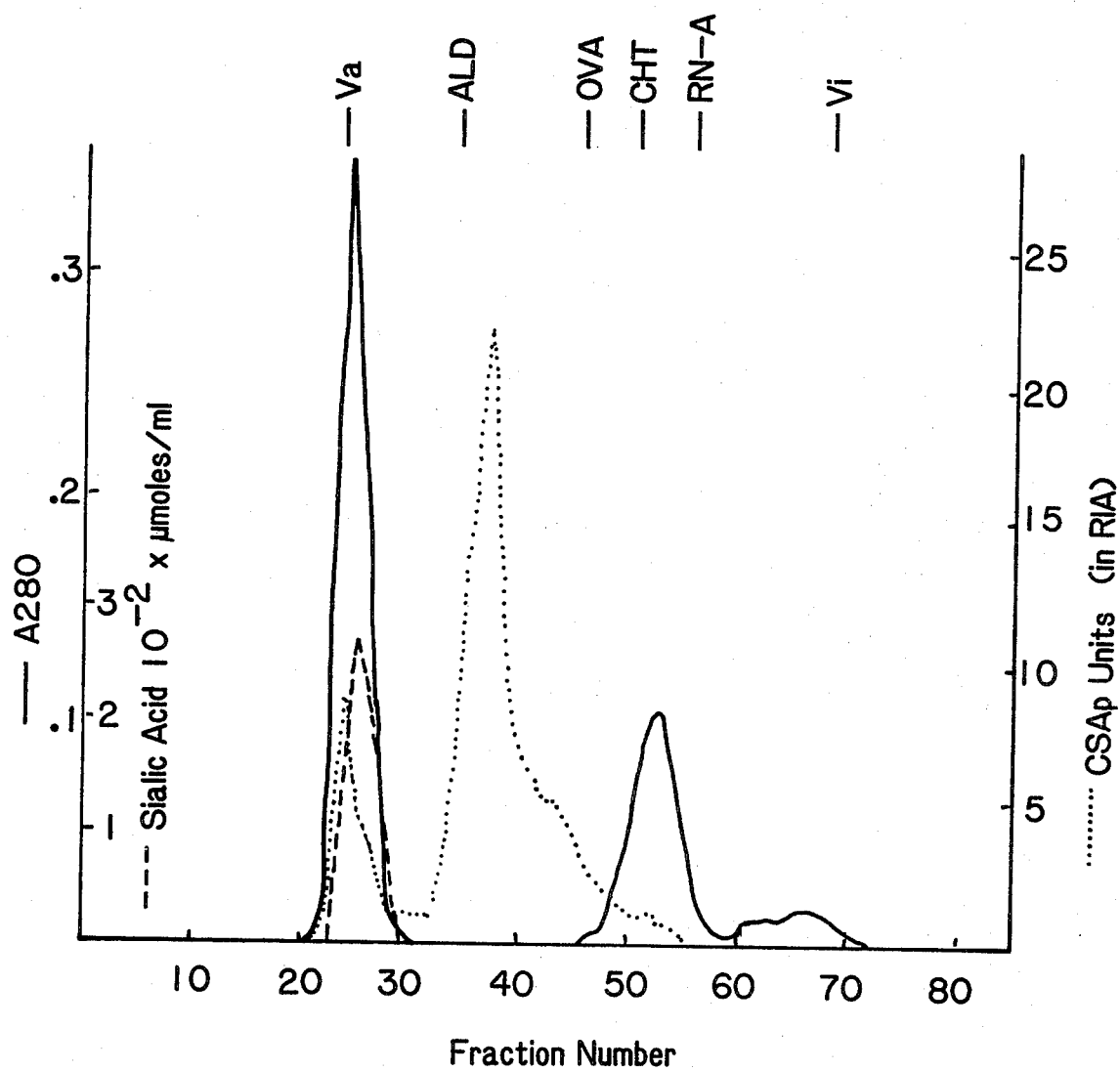
FIG. 1 is a plot of the fractions eluted by chromatography of the tryptic digest of CSAp on Sepharose CL-4B.

In contrast to earlier work assigning the molecular size of CSAp to a range between 70,000 and 120,000, it has now been found that native CSAp is a large molecular size antigen, having a molecular weight of about four million. Native CSAp is likely to be a glycoprotein since it binds to concanavalin A. In this respect, CSAp is different from gastrointestinal mucins which contain only trace amounts of mannose. Furthermore, neither CMA nor ZGM bind to concanavalin A.

It has also been found that CSAp is destroyed by phenol or perchloric acid extraction, in which respect it differs from other gastrointestinal antigens such as CEA, CMA, CSA and human intestinal goblet cell antigen (GOA). CSAp is sensitive to thiolic (sulfhydryl) reagents, even in low concentrations, indicating that the CSAp antigenic determinant is associated with the polypeptide chain rather than with a carbohydrate moiety. High concentrations of chaotropic reagents also inactivate CSAp. Attempts to dissociate intact native CSAp from the void fraction of gel filtration chromatography by treatment with solutions of high ionic strength, sodium dodecyl sulfate (SDS), non-ionic detergents and 1 M lithium bromide were unsuccessful.

The susceptibility of CSAp to various chemicals is shown in Table 1.

TABLE 1
SUSCEPTIBILITY OF CSAp ACTIVITY TO VARIOUS CHEMICALS

| Reagent | Concentration | Duration of Exposure (hr)$^a$ | Residual Activity (% of original)$^b$ |
|---|---|---|---|
| Ethanol | 70% | <1 | 100 |
| Dithiothreitol | 2 mM | 3 | <1 |
| " | 20 mM | 3 | 0 |
| Sodium Dodecyl Sulfate | 1% | up to 24 | 100 |
| Octyl-$\beta$-D-glucopyranoside | 30 mM | up to 24 | 100 |
| Lithium Bromide | 1 M | up to 24 | 100 |
| " | 3 M | 3 | 50 |
| Potassium Thiocyanate | 3 M | 3 | 25-50 |
| Ammonium Thiocyanate | 3 M | 3 | 50 |
| Ammonium Iodide | 3 M | 3 | 50 |
| Sodium Iodide | 3 M | 3 | 50 |
| Urea | 6 M | 3 | 50 |

TABLE 1-continued

SUSCEPTIBILITY OF CSAp ACTIVITY TO VARIOUS CHEMICALS

| Reagent | Concentration | Duration of Exposure (hr)[a] | Residual Activity (% of original)[b] |
|---|---|---|---|
| Guanidine-HCl | 4 M | 3 | 25–50 |
| Sodium Perchlorate | 3 M | 3 | 25 |

[a]Following the incubation the reagent was removed by extensive dialysis at 4° C.
[b]Tested by HAI assay.

Sonication of a CSAp solution produced a heterogeneous mixture of lower molecular weight compounds, some of which retained CSAp immunological reactivity. However, isolation of a pure, homogeneous lower molecular weight CSAp-active antigen by this means was impractical.

Accordingly, a method has been developed for producing an immunologically active fragment which can be purified and which is substantially homogeneous. This is successfully achieved by means of partial tryptic digestion of high molecular weight native CSAp. A purified, immunologically active tryptic peptide having CSAp antigenic activity is obtained thereby.

Tissue Extraction and Fractionation of GW39 Tumor CSAp

GW-39 tumors, serially transplanted in unconditioned hamsters by the method of Goldenberg et al, *Transplantation*, 4, 760 (1966), are excised 6 to 8 weeks after transplantation and stored at −20° C. until used. Alternatively, normal colon tissue, other human colon cancers, pancreatic cancers, or cyst fluid from ovarian mucinous cystadenocarcinomas may be used as sources of CSAp, and treated analogously to GW-39 tissue. Human tumors in cell culture or transplanted in animals may also serve as a source of CSAp.

Minced frozen tumors are mixed with several volumes, e.g., 5 volumes (1 g/5 ml), of cold 0.3–3 M aqueous salt solution and homogenized on ice, e.g., in an Omnimixer (Sorvall Inc., Newtown, Conn.). Preferably, the salt solution contains sodium chloride and 0.05–0.2 M ammonium bicarbonate, most preferably about 0.5 M NaCl and about 0.1 M $NH_4HCO_3$. Minor modification of these salts or buffers is also possible, although phosphate buffers tend to promote aggregation of the protein, and trailing on the column with a more diffuse elution profile. Homogenization is preferably effected at full speed for two periods of two minutes each, interrupted by a two-minute cooling period. The homogenate is centrifuged at about 48,000×g for 30–60 minutes, preferably about 40 minutes, at 1–20° C., preferably 1–6° C., most preferably about 4° C. The floating lipid layer is removed from the surface of the aqueous phase by suction, and the supernatant aqueous phase is collected and, preferably, recentrifuged under the same condition, e.g., for an additional 20 minutes.

The final supernatant is fractionated by gel filtration on a column permitting separation of protein molecules by molecular weight. Suitable such media include gels prepared by crosslinking polysaccharides, e.g., agarose. Preferably, the fractionation is effected by gel filtration on Sepharose CL-4B columns (Pharmacia Fine Chemicals, Inc., Piscataway, N.J.). Preferably, the column is equilibrated prior to fractionation in the same buffer used for tissue extraction. Advantageously, columns of 5×100 cm and 2.6×100 cm are used for preparative purposes, while smaller columns, e.g., 1.5×90 cm are used for pilot experiments and analytical studies.

Sample volumes are advantageously 1 to 1.4% of the total column volume, and specific flow rates advantageously range from 5 to 7 ml/hour×$cm^2$.

The fractions collected are advantageously equal to the sample volumes, except for the largest preparative columns. The eluents are monitored, e.g., by measuring absorption at a wavelength of 280 nm, and the fractions are analyzed for the presence of CSAp. Suitable analytical methods for detecting the presence of CSAp include hemagglutination-inhibition assay (HAI assay) or radioimmunoassay (RIA). These are described in more detail below.

Examination of the individual fractions of the eluent revealed that more than 90% of the CSAp activity is associated with the void volume fraction, at a molecular size of 4 million or more. Less than 10%, and usually about 3%, of the CSAp activity is eluted as smaller molecular size material. When this smaller CSAp entity is compared by immunodiffusion with the void fraction CSAp, a precipitin line of identity against CSAp antibody is obtained. Apparently, this lower molecular size CSAp results from breakdown of native CSAp during homogenization. The low molecular size CSAp material is heterogeneous, and is present in all fractions corresponding to molecular sizes ranging from 70,000 to 800,000.

The void volume fraction is concentrated to the original sample volume. Initial attempts to effect concentration by ultrafiltration through an ultrafiltration membrane, e.g., Amicon membranes (Amicon Corp., Lexington, Mass.), resulted in loss of native CSAp. Concentration without the use of high pressure may be successfully effected using dialysis membranes which are contacted at their outside surfaces with a water-absorbent material, preferably a hygroscopic compound such as an anhydrous carbohydrate polymer. Suitable such polymers are dry polydextrans and, preferably, the sodium salt of carboxymethylcellulose, which is available commercially as Aquacide (Calbiochem-Behring corp., La Jolla, Calif.). The Aquacides are available in several grades, Aquacide II-A, corresponding to a molecular weight of about 500,000, being particularly well suited for rapid dehydration of the solution contained in a dialysis membrane. It is useful to further dialyze the concentrated void fraction against appropriate buffer to eliminate any materials which may possibly be leached from the Aquacide or other dehydrating agent.

As noted above, CSAp levels may be estimated by either an HAI assay or an RIA assay. The detailed procedures below are illustrative, and may be modified in ways which will be apparent to one of ordinary skill in the art.

Antibody preparation for HAI and RIA

Antiserum to the unfractionated GW-39 tumor's 48,000×g supernatant, prepared as described above, was raised in goats, and monospecific anti-CSAp immunoglobulin G was obtained following a series of affinity adsorptions as described in detail by Gaffar et al., *Int. J. Cancer*, 27, 101, (1981). Briefly, the immunoglobulin fraction was obtained by chromatography of the goat antiserum on a column of human colon cancer extract bound to Sepharose 4B. The final purification was achieved by processing the 3M $NH_4SCN$ eluate from this column through the following three immunoadsorbent columns:

1. Human tissue extracts (spleen, lung and plasma);
2. hamster tissue extracts (liver, kidney and plasma); and
3. phenol-water extracts of GW-39 tumor. The anti-CSAp antibody thus obtained showed a single precipitin line when reacted in gel diffusion with extracts of human colonic carcinoma and GW-39 tumor. No reactivity was detected against normal human and hamster lung, liver, spleen, kidney and muscle extracts, and plasma.

Hemagglutination-inhibition (HAI) assay for CSAp

The HAI assay was performed essentially as described by Pant et al, *Immunol. Commun.*, 6, 441 (1977), with the following modification in the preparation of sensitized sheep erythrocytes. GW-39 tumor tissue was homogenized in 5 volumes of ice cold deionized water, the 48,000×g supernatant was collected and sonicated for 6 min (4×1.5-min cycles) in an ice bath, and then acidified to pH 4.8 to 5.0 by dropwise addition of 0.5 N HCl. The insoluble material formed was removed by centrifugation at 12,000×g at 4° C. for 20 min, and 10 to 15 ml of clear supernatant were added to 0.5 ml formalinized sheep erythrocytes that had been prepared according to the procedure of Csizmas, *Proc. Soc. Exptl. Biol. Med.*, 103, 157 (1960). The mixture was reacted for 60 min at room temperature with occasional mixing. The sensitized red blood cells were pelleted at 1,000×g for 10 min, washed 3 times with 20 volumes of phosphatebuffered normal saline (2mM sodium phosphate, pH 7.2) and dispensed in the same buffer to form a 0.6% (v/v) suspension; 0.01% sodium azide was added as a preservative. The HAI test was carried out in Cooke microtiter U plates. Dilutions of the assayed antigen were made by serial dilution of 25 $\mu$l antigen in 25 $\mu$l of 2% normal goat serum in phosphate-buffered saline (10 mM sodium phosphate, pH 7.2) placed in each well, and then adding 25 $\mu$l anti-CSAp goat antiserum as prepared above, and properly diluted to represent 2 hemagglutination units. The plate was sealed, mixed, and incubated for 60 min at 37° C. Subsequently, 25 $\mu$l of sensitized sheep erythrocytes were added to each well and the plate was resealed, mixed, and left to develop at room temperature. The results were recorded after 4 to 6 hr and again after settling overnight.

Radioimmunoassay (RIA) of CSAp

CSAp immunoadsorbent was prepared by binding the 48,000×g supernatant of the GW-39 tumor homogenate as prepared above to polyvinylidene fluoride powder, e.g., Kynar, grade 301F (Penwalt Corp., King of Prussia, PA.), according to the method of Newman et al., *Proc. Am. Assoc. Cancer Res.*, 21, 218 (1980). A volume of 12.5 ml of the supernatant was added to 1 g of activated Kynar. The anti-CSAp antibody was radiolabeled with $^{125}$I (Amersham Searle, Arlington Heights, Ill.) to a specific activity of 10.2 Ci/g by the chloramine-T procedure of Greenwood et al, *Biochem. J.*, 89, 114 (1963). The immunoadsorbent bound about 60% of the labeled antibody preparation. In 13×100 mm disposable glass tubes, 100 $\mu$l of the assayed antigen, 100 $\mu$ of diluted antiserum containing 50,000 cpm, and 1 ml of 1% goat serum in phosphate-buffered saline (10 mM sodium phosphate, pH 7.2) were combined. The tubes were mixed and incubated at 37° C. for 90 min and then 1 ml washed immunoadsorbent (2% Kynar suspension) was added to each, mixed well, and incubated with periodic agitation for an additional hour at 37° C. At the end of the incubation the tubes were centrifuged at 900×g for 10 min, the supernatant was discarded, the pellet was resuspended in 1 ml of 1% goat serum in phosphate-buffered saline (10 mM in phosphate, pH 7.2), and then centrifuged again. After decanting the supernatant the amount of radio-labeled antibody bound to the immuno-adsorbent was determined in, e.g., a Packard (Downers Grove, Ill.) Model 5230 gamma scintillation counter. The sonicated GW-39 tumor's 48,000×g supernatant served as a standard. The stock supernatant was divided into 0.5 ml aliquots and stored at $-20°$ C. New standards were always compared with old ones before use. To quantify CSAp, a series of dilutions from each sample are analyzed and the $B/B_o\%$ values (where B is $^{125}$I bound to the immunoadsorbent in the presence of antigen and $B_o$ in its absence) are plotted versus the dilution, and the dilution factors which are needed to bring the $B/B_o\%$ values to 60% or 70% are compared. The dilution of the standard which resulted in approximately 92% of maximum binding (the range spreads between 90% to 94%) is selected as one CSAp unit. On a weight basis one CSAp unit represents between 4.5 and 9.0 ng protein of the Sephadex G-200 column-purified tryptic peptide preparation, or 200 ng unfractionated 48,000×g supernatant.

Partial Tryptic Digestion of Native CSAp

The concentrated void volume fraction, as prepared above, advantageously containing from 300 to 500 $\mu$g of protein, per ml of aqueous 0.06-3.5 M salt solution, e.g. 0.05-0.5 M, preferably about 0.1 M $NH_4HCO_3$ and 0.1-3 M, preferably about 0.15 M NaCl, and preferably containing about 0.02% sodium azide, is digested with trypsin. Other salts and buffers may be used, provided they achieve a pH suitable for trypsin activity, preferably pH 7.5-8.5, and most preferably pH 8.0-8.1. Advantageously, the trypsin is present at a relative concentration of 0.5-7% by weight relative to the CSAp to be digested, preferably about 5% by weight. The trypsin is advantageously diphenyl carbamyl chloride-treated trypsin (Sigma Chemical company, St. Louis, Mo.). Digestion is effected for, e.g., 1-8 hours, more preferably 4.5-5.5, most preferably about 5 hours, at a temperature of 15-45° C., preferably about 37° C., for minimal losses.

The reaction is terminated by addition of an effective inhibitor, e.g., commercially available soybean trypsin inhibitor (Sigma), or, preferably, a non-protein trypsin inhibitor, e.g., N-$\alpha$-p-tosyl-L-lysine chloromethyl ketone.HCl, at about 10 mM final concentration, or phenylmethylsulfonyl fluoride (PMSF) in dimethylformamide (DMF) at about 10% (V/V) final DMF concentration and about 5 mM final PMSF concentration. The efficacy of the trypsin inhibition is monitored in each digest using, e.g., the casein-agarose plate protease detection assay (BioRad, Richmond, Calif.).

CSAp is reduced in size by the partial tryptic digestion. CSAp antigenicity exhibits remarkable resistance to proteolysis. After incubation of the void volume fraction as described above, only 25-35% of the original CSAp activity is lost, as determined by comparison of the undigested and digested void volume fractions by RIA.

Fractionation of the digestion product on Sepharose CL-4B reveals that the majority of the antigen is reduced to smaller fragments which elute closer to the included volume rather than to the excluded volume of the column. Better fractionation is achieved on a Sephadex G-200 column, by means of which 80-87% of the residual CSAp activity is eluted in a section of the chromatogram that is substantially lacking in absorbence at 280 nm.

The distribution of the CSAp activity in the fractions obtained by chromatography of a 2 ml sample of the tryptic digest on Sephadex G-200 (1.5×90 cm), eluted with 0.1 M NH$_4$HCO$_3$ containing 0.15 M NaCl, at a flow rate of 10 ml/hr at room temperature is shown in FIG. 1. Fractions of 2 ml were collected. The solid line in the figure denotes the absorbence at 280 nm; the dashed line shows the sialic acid content; and the dotted line shows the CSAp activity. The arrows mark the elution volumes of substances used for calibration of the column. $V_O$ void volume (Dextran Blue); $V_I$ included volume ($^{125}$I); ALD, aldolase; OVA, ovalbumin; CHT, α-chymotrypsinogen-A; RN-A, ribonuclease A. The values in the figure for CSAp activity were calculated by integrating the CSAp inhibitory activity in a RIA in each one of the individual fractions collected. The sialic acid determination was effected by the thiobarbituric acid method of Warren, *J. Biol. Chem.*, 234, 1971 (1959).

Enzymatic cleavage of CSAp by trypsin is specific and produces two distinct peptides, one of them presumably being the precursor of the other. The exact sequence of the proteolytic cleavage is as yet unknown. Following proteolysis, the tryptic peptides having CSAp activity elute well after the bulk of the sialic acid, while the 48,000×g GW-39 supernatant has sialic acid associated with the fraction containing CSAp activity. This behavior is in contrast to CMA, in which the antigenic determinants are associated with the fraction containing sialic acid even after extensive digestion with either trypsin or pronase.

The tryptic digestion sometimes forms a single lower molecular weight peptide and sometimes produces a small amount, occasionally as much as 25%, of another peptide. The major peptide has an apparent molecular size of about 120,000. This major tryptic peptide is found to be immunologically identical to native CSAp by double gel diffusion studies conducted according to the method of Ouchterlony, *Progr. Allergy*, 5, 1 (1958).

The result is confirmed by immunoelectrophoresis in agarose. Polyacrylamide gel electrophoresis was carried out in 7% acrylamide cylindrical gels with stacking gels as prescribed for System I, formula 1 and 2, by Gabriel, *Methods Enzymol.*, 22, 565 (1971). Samples of approximately 1 μg of protein were applied to the gels, but they could not be visualized by staining with coomassie blue or periodic acid-Schiff base reagent. However, the CSAp zones could be detected immunologically.

The polyacrylamide cylindrical gels were sliced longitudinally in quarters, one slice was embedded in 1% agarose and reacted with anti-CSAp antibody placed in a parallel trough at room temperature for 24 hours. The agarose gels were made in sodium barbital buffer, pH 8.6, ionic strength 0.05. A constant current of 5.5 mA was used per 2.5×7.6 cm glass plate covered with 3 ml gel. After reaction, the acrylamide gel was then removed and the agarose plate was washed, dried, and finally stained with 0.5% amido-black in 7% acetic acid.

In the cases where only one lower molecular weight tryptic peptide is produced, it has the slower anodic migration compared to the second peptide produced as a minor component in those cases where two tryptic peptides are produced. In order to determine the width of the zones and the distribution of CSAp among the peptides, the gels were sliced transversely into 1.5 mm discs and eluted overnight at 4° C. into 250-400 μl phosphate-buffered saline (10 m M in phosphate, pH 7.2) containing 0.02% sodium azide. The amounts of CSAp in the eluents were quantified later by RIA, and it was found that the width of each pedtide's zone did not exceed two gel slices (3 mm), and that the peptide closer to the cathode usually contained approximately 90% of the CSAp activity, and in no case less than 75%.

Fractions containing tryptic peptides can be concentrated by ultrafiltration on ultrafiltration membranes, e.g., Amicon YM-10 membranes (Amicon Corp., Lexington, Mass.), or by the process described above, using a dialysis membrane and a hygroscopic material, e.g., Aquacide II-A, with comparable recoveries. Unfortunately, losses of these CSAp tryptic peptides during concentration are substantial, regardless of whether ultrafiltration or dialysis/hygroscopic materials is used for concentration. Lyophylization was also tried, but it failed to improve the recovery. However, it is possible to increase the recoveries up to 16-fold by the addition of a small amount of goat serum (10% final concentration) to the pooled column fractions prior to concentration.

An average of about 9.1% of the initial CSAp activity is recovered as Sephadex G-200 column-purified tryptic peptide, while achieving a 35-fold purification. The purification steps for the CSAp tryptic peptides are summarized in Table 2.

TABLE 2

SUMMARY OF PURIFICATION STEPS FOR CSAp TRYPTIC PEPTIDES

| | Volume (ml) | Total CSAp activity (units)$^a$ | Total protein (μg) | Specific activity (units/μg) | Recovery (%) | Purification Factor |
|---|---|---|---|---|---|---|
| Tumor extract (48,000 × g supernatant) | 2 | 40,384 | 6,916 | 5.8 | 100 | 0 |
| Void fraction (Sepharose CL-4B column) | 2 | 28,551 | 588 | 48.6 | 70.7 | 8 |
| Tryptic peptides (Sephadex G-200 column) | 4 | 3,680 | 18 | 204.4 | 9.1 | 35 |

$^a$CSAp inhibitory activity in RIA.

Anti-CSAp Antibodies from Tryptic Peptide

The procedure described above for producing anti-CSAp is repeated, except that the antigen used is the 120,000 molecular weight tryptic peptide in the form of its solution obtained by concentration of pooled Sephadex G-200 fractions. The remainder of the procedure is the same, and a good yield of highly monospecific anti-CSAp antibodies is produced. CSAp-specific antibodies may also be produced by the hybridoma technique, where, e.g., rodents or subhuman primates are immunized with the CSAp tryptic peptide and then the lymphocytes are fused with rodent or human myeloma cells, resulting in hybrid cells producing CSAp antibodies.

The procedures described above may be modified by the use of equivalent or analogous reagents, conditions or procedures in a manner well known to the skilled art worker. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for producing a purified, substantially homogeneous immunologically active tryptic peptide having colon-specific antigen-p (CSAp) antigenic activity, comprising the steps of:
   (a) enzymatically partially digesting a native CSAp fraction, having a molecular weight of at least about 4 million, with trypsin for 1–8 hours, and terminating the digestion with a trypsin inhibitor, the efficacy thereof being monitored by determining the substantial absence of residual protease activity; and
   (b) fractionating the partial tryptic digest, and recovering at least one substantially homogeneous fraction containing a tryptic peptide having CSAp antigenic activity, having a molecular weight of about 120,000 and having substantially no absorbance at 280 nm.

2. The method of claim 1, wherein said trypsin inhibitor is a non-protein trypsin inhibitor.

3. The method of claim 1, wherein said trypsin inhibitor is N-α-p-tosyl-L-lysine chloromethyl ketone hydrochloride.

4. A method for producing a purified, substantially homogeneous immunologically active tryptic peptide having colon-specific antigen-p (CSAp) antigenic activity, comprising the steps of:
   (a) homogenizing CSAp-containing tissue in cold 0.3–3M aqueous salt solution:
   (b) centrifuging the resultant homogenate, removing the floating lipid layer, and recovering the aqueous supernatant;
   (c) fractionating the recovered aqueous supernatant by gel filtration, and recovering and concentrating at least one fraction containing a CSAp having a molecular weight of at least about 4 million;
   (d) enzymatically partially digesting the concentrated CSAp fraction from step (c) with trypsin for 1–8 hours, and terminating the digestion with a trypsin inhibitor, the efficacy thereof being monitored by determining the substantial absence of residual protease activity; and
   (e) fractionating the partial tryptic digest, and recovering at least one substantially homogeneous fraction containing a tryptic peptide having CSAp antigenic activity, having a molecular weight of about 120,000 and having substantially no absorbance at 280 nm.

5. The method of claim 4, wherein the CSAp-containing tissue is normal human colon, human colonic tumor, human intestinalized gastric tumor, human pancreatic tumor, or cyst fluid from human ovarian mucinous cystadenocarcinoma.

6. The method of claim 4, wherein in step (a), the salt is sodium chloride.

7. The method of claim 6, wherein the aqueous salt solution further contains 0.05–0.2 M ammonium bicarbonate.

8. The method of claim 4, wherein in step (c), the CSAp-containing fractions are pooled and concentrated in dialysis membranes using a hygroscopic compound to absorb water passing to the outside of the membrane.

9. The method of claim 4, wherein in step (d), the partial tryptic digestion is effected in an aqueous pH 7.5–8.5 buffer solution at about 37° C. for 4.5–5.5 hours.

10. The method of claim 9, wherein the aqueous buffer is 0.01–3 M in NaCl and 0.05–0.5 M in NH$_4$HCO$_3$; and the trypsin is present at a relative concentration of 0.5–7% by weight relative to the CSAp to be digested.

11. The method of claim 4, wherein in step (e), the fractions containing a tryptic peptide having CSAp antigenic activity are pooled and concentrated by ultrafiltration through ultrafiltration membranes or in dialysis membranes using a hygroscopic compound to absorb water passing to the outside of the membrane.

12. The method of claim 11, wherein in step (e), goat serum is added to said pooled fractions prior to concentration.

13. The method of claim 12, wherein said trypsin inhibitor is a non-protein trypsin inhibitor.

14. The method of claim 13, wherein said trypsin inhibitor is N-α-p-tosyl-L-lysine chloromethyl ketone hydrochloride.

15. The method of claim 4, wherein said trypsin inhibitor is a non-protein trypsin inhibitor.

16. The method according to claim 15, wherein said trypsin inhibitor is N-α-p-tosyl-L-lysine chloromethyl ketone hydrochloride.

17. The method of claim 15, wherein said trypsin inhibitor is phenylmethylsulfonyl fluoride.

18. In a method for producing substantially monospecific antibodies to colon-specific antigen-p (CSAp), comprising the steps of:
   (a) raising antibodies in an animal by challenging the animal with an antigen having CSAp antigenic activity, and recovering antiserum from the animal;
   (b) purifying the antibodies by affinity chromatography on a human colon cancer immunoabsorbent column, and then on immunoabsorbent columns containing bound antigens from human spleen, lung and plasma extracts, from hamster liver, kidney and plasma extracts, and from phenol-water extracts of GW-39-tumor; thereby removing species-specific and crossreactive antibodies against normal tissue antigens, and antibodies against non-phenol-labile colon-specific antigens; and
   (c) freeing the resultant antibodies from any antibody aggregates formed during the purification procedure, and recovering monospecific anti-CSAp antibodies,
   the improvement wherein said antigen is a substantially homogeneous tryptic peptide produced by a method comprising the steps of:
   (i) enzymatically partially digesting a native CSAp fraction, having a molecular weight of at least about 4 million, with trypsin for 1–8 hours, and terminating the digestion with a trypsin inhibitor, the efficacy thereof being monitored by determining the substantial absence of residual protease activity; and
   (ii) fractionating the partial tryptic digest, and recovering at least one substantially homogeneous fraction containing a tryptic peptide having CSAp antigenic activity, having a molecular weight of about 120,000 and having substantially no absorbance at 280 nm.

19. A reaction mixture from partial tryptic digestion of a native CSAp fraction, comprising: (1) a tryptic peptide having CSAp antigenic activity, having a molecular weight of about 120,000 and having substantially no absorbance at 280 nm; (2) trypsin; and (3) an effective inhibiting amount of a trypsin inhibitor.

* * * * *